US011104925B2

(12) United States Patent
Lee et al.

(10) Patent No.: US 11,104,925 B2
(45) Date of Patent: Aug. 31, 2021

(54) MICROORGANISM PRODUCING L-LYSINE AND METHOD FOR PRODUCING L-LYSINE USING THE SAME

(71) Applicant: CJ CHEILJEDANG CORPORATION, Seoul (KR)

(72) Inventors: Peter Lee, Suwon-si (KR); Hyung Joon Kim, Seoul (KR); Hyang Choi, Suwon-si (KR); Song Gi Ryu, Suwon-si (KR); Sang Mok Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 29 days.

(21) Appl. No.: 15/741,392

(22) PCT Filed: Jun. 27, 2016

(86) PCT No.: PCT/KR2016/006833
§ 371 (c)(1),
(2) Date: Jan. 2, 2018

(87) PCT Pub. No.: WO2017/007159
PCT Pub. Date: Jan. 12, 2017

(65) Prior Publication Data

US 2018/0195097 A1 Jul. 12, 2018

(30) Foreign Application Priority Data

Jul. 3, 2015 (KR) ........................ 10-2015-0095528

(51) Int. Cl.
*C12P 13/08* (2006.01)
*C12N 15/77* (2006.01)
*C07K 14/34* (2006.01)

(52) U.S. Cl.
CPC .............. *C12P 13/08* (2013.01); *C07K 14/34* (2013.01); *C12N 15/77* (2013.01)

(58) Field of Classification Search
None
See application file for complete search history.

(56) References Cited

U.S. PATENT DOCUMENTS

2005/0191732 A1* 9/2005 Pompejus .............. C07K 14/34 435/106
2007/0254345 A1 11/2007 Fukui et al.

FOREIGN PATENT DOCUMENTS

| | | | |
|---|---|---|---|
| JP | 2007-151551 | A | 6/2007 |
| JP | 2012-530515 | A | 12/2012 |
| KR | 94-0001307 | B1 | 2/1994 |
| KR | 10-0159812 | | 8/1998 |
| KR | 10-0838035 | B1 | 6/2008 |
| KR | 10-0924065 | B1 | 10/2009 |

OTHER PUBLICATIONS

Baumgart et al. , Applied and Environmental Microbiology, vol. 79, pp. 6006-6015, Oct. 2013.*

Sekiguchi, "Comprehensive research on bacterial cell wall degradation and modification enzymes," *Seibutsu-kogaku* 91:50-72, with English abstract (26 pages) (2013).

Binder et al., "A high-throughput approach to identify genomic variants of bacterial metabolite producers at the single-cell level," *Genome Biology* 13:R40 (12 pages) (2012).

Mellroth et al., "LytA, Major Autolysin of *Streptococccus pneumoniae*, Requires Access to Nascent Peptidoglycan," *Journal of Biological Chemistry* 287(14):11018-11029 (Mar. 30, 2012).

Moore et al., "Photometric Ninhydrin Method for use in the Chromatography of Amino Acids," *Journal of Biological Chemistry* 176:367-388 (1948).

Nakamura et al., "Mutations of the *Corynebacterium glutamicum* NCgl1221 Gene, Encoding a Mechanosensitive Channel Homolog, Induce $_L$-Glutamic Acid Production," *Applied and Environmental Microbiology* 73(14):4491-4498 (Jul. 2007).

Olrichs "Bugging the cell wall of bacteria—Novel insights into peptidoglycan biosynthesis and its inhibition," *Utrecht University* p. 1-136 (2010).

Rice et al., "Molecular Control of Bacterial Death and Lysis," *Microbiology and Molecular Biology Reviews* 72(1):85-109 (Mar. 2008).

Xu et al., "Metabolic engineering *Corynebacterium glutamicum* for the $_L$-lysine production by increasing the flux into $_L$-lysine biosynthetic pathway," *Amino Acids* 46:2165-2175 (2014).

Tsuge et al., "Deletion of cgR_1596 and cgR_2070, Encoding N1pC/P60 Proteins, Causes a Defect in Cell Separation in *Corynebacterium glutamicum* R," *Journal of Bacteriology* 190(24):8204-8214 (Dec. 2008).

* cited by examiner

*Primary Examiner* — Richard G Hutson
(74) *Attorney, Agent, or Firm* — Seed IP Law Group LLP

(57) ABSTRACT

The present disclosure relates to a microorganism producing L-lysine and a method for producing L-lysine by using the same. More specifically, the present disclosure relates to a microorganism of the genus *Corynebacterium*, which is modified such that the activity of a protein involved in cell wall hydrolysis is inactivated in comparison with the endogenous activity thereof; and a method for producing L-lysine using the same.

2 Claims, No Drawings

Specification includes a Sequence Listing.

SEQUENCE LISTING

```
<160> NUMBER OF SEQ ID NOS: 26

<210> SEQ ID NO 1
<211> LENGTH: 604
<212> TYPE: PRT
<213> ORGANISM: Corynebacterium sp
<220> FEATURE:
<221> NAME/KEY: PEPTIDE
<222> LOCATION: (1)...(604)
<223> OTHER INFORMATION: NCgl1480

<400> SEQUENCE: 1

Met Thr Arg Ala Leu Ile Ala Leu Ala Val Ser Gly Ala Leu Leu Ser
1               5                   10                  15

Ser Met Thr Pro Ala Val Ala Gln Pro Gln Asn Pro Asp Asp Ala Ala
            20                  25                  30

Ile Ala Gln Ala Glu Glu Asn Val Ser Ala Gly Asp Gly Glu Val Ala
        35                  40                  45

Arg Leu Ala Gly Ser Leu Ser Ser Thr Asp Ala Glu Ile Asn Arg Val
    50                  55                  60

Glu Leu Glu Met Gly Ala Leu Arg Glu Glu Val Asn Lys Ser Leu Val
65                  70                  75                  80

Asp Leu His Asp Ala Gln Ala Ile Ala Glu Gln Ala Arg Gln Asp Ala
                85                  90                  95

Leu Ala Ala Lys Lys Asp Leu Asp Asp Ser Gln Ala Gln Ile Glu Ala
            100                 105                 110

Ala Gln Glu Arg Leu Asp Glu Ile Ser Arg Ala Ala Tyr Arg Gln Asn
        115                 120                 125

Gly Thr Ser Lys Gly Leu Ser Gly Ile Ser Gly Asn Gly Asn Ser Glu
    130                 135                 140

Asp Ala Leu Asp Arg Gln Thr Tyr Leu Arg Thr Ser Ala Glu Lys Gln
145                 150                 155                 160

Gln Ala Ala Val Glu Glu Leu Asp Arg Leu Arg Thr Glu Asn Ala Asn
                165                 170                 175

Lys Glu Ser Val Leu Arg Gln Ala Arg Ile Val Ala Glu Gln Arg Glu
            180                 185                 190

Ala Glu Ala Val Glu Lys Gln Val Gln Thr Glu Ala Ala Ile Ala Ala
        195                 200                 205

Asn Ser Glu Gln Leu Asn Val Leu Thr Asn Asn Arg Ser Thr Leu Val
    210                 215                 220

Ala Gln Arg Asp Gly Ala Glu Arg Asn Leu Ala Ile Ala Arg Ala Gln
225                 230                 235                 240

Ala Asp Asn Leu Gln Gly Gln Arg Ala Glu Tyr Glu Glu Phe Gln Gln
                245                 250                 255

Ala Glu Gln Ala Arg Ile Gln Ala Glu Ala Glu Ala Gln Ala Ala Ala
            260                 265                 270

Glu Glu Lys Arg Arg Ala Asp Glu Ala Ala Ala Gln Ala Ala Ala Glu
        275                 280                 285

Ala Gln Glu Ala Ala Gln Gln Ala Gln Ala Ala Glu Glu Ala Gln Ala
    290                 295                 300
```

-continued

```
Ala Gln Ala Ala Glu Thr Ala Gln Ala Gln Ala Ala Gln Ala Ala Glu
305                 310                 315                 320

Thr Gln Ala Ala Gln Ala Ala Gln Ala Gln Ala Glu Ala Asn Asp Arg
                325                 330                 335

Ala Ala Ala Gln Gln Arg Ala Ala Glu Ala Gln Ala Ala Ala Glu Gln
            340                 345                 350

Ala Gln Arg Glu Ala Asp Ala Gln Ala Ala Asn Asp Ala Gln Ala Gln
        355                 360                 365

Ala Leu Arg Glu Gln Ala Leu Thr Ala Ala Ser Ile Ala Ala Ala Ala
    370                 375                 380

Leu Ile Ala Ala Ser Gln Ser Ser His Ala Thr Thr Gln Asn Pro Tyr
385                 390                 395                 400

Pro Thr Asp Glu Asp Ala Asp Pro Thr Asp Ile Ala Asp Ile Gln Gly
                405                 410                 415

Pro Thr Gln Pro Gly Thr Gly Glu Ser Gly Asp Ser Gln Ser Asn Ser
            420                 425                 430

Ser Asp Asn Asp Ser Thr Gly Asn Asp Ser Thr Gly Ser Asp Ser Ser
        435                 440                 445

Asp Ser Asp Ser Ser Gly Asn Asp Ser Ser Glu Val Ile Ser Gly Asp
    450                 455                 460

Arg Ser Ala Gln Ile Glu Thr Val Ile Ala Arg Ala Met Ser Gln Leu
465                 470                 475                 480

Gly Val Gln Tyr Ala Trp Gly Gly Gly Asn Ala Asn Gly Pro Thr Leu
                485                 490                 495

Gly Ile Arg Asp Gly Gly Val Ala Asp Ser Tyr Gly Asp Tyr Asn Lys
            500                 505                 510

Val Gly Phe Asp Cys Ser Gly Leu Thr Leu Tyr Ala Phe Ala Gly Val
        515                 520                 525

Gly Ile Ser Leu Pro His Tyr Thr Gly Tyr Gln Tyr Gln His Gly Thr
    530                 535                 540

Lys Val Ser Pro Ser Glu Met Gln Arg Gly Asp Leu Ile Phe Tyr Gly
545                 550                 555                 560

Pro Gly Ala Ser Gln His Val Ala Ile Tyr Leu Gly Asp Gly Gln Met
                565                 570                 575

Ile Glu Ala Pro Asn Ser Gly Ser Val Val Lys Ile Ser Pro Val Arg
            580                 585                 590

Trp Ser Gly Met Thr Glu Ser Val Val Arg Leu Ile
        595                 600
```

<210> SEQ ID NO 2
<211> LENGTH: 349
<212> TYPE: PRT
<213> ORGANISM: Corynebacterium sp
<220> FEATURE:
<221> NAME/KEY: PEPTIDE
<222> LOCATION: (1)...(349)
<223> OTHER INFORMATION: NCgl2107

<400> SEQUENCE: 2

```
Met Asn Glu Val Asp Arg Gly Phe Leu Lys Met Phe Gly Arg Arg Trp
1               5                   10                  15

Val Ser Val Val Ala Ser Cys Val Ile Ala Ser Thr Leu Ile Leu Val
            20                  25                  30

Pro Ser His Ser Gly Ala Glu Glu Val Asp Gln Leu Ile Ala Asp Ile
        35                  40                  45

Glu His Val Ser Gln Glu Thr Ser Ala Gln Asn Glu Glu Val Lys Gln
```

-continued 50 55 60

Leu Glu Ile Asp Ile Glu Ala Arg Glu Val Thr Ile Lys Glu Val Gln
65 70 75 80

Glu Gln Ser Val Ser Tyr Arg Glu Ala Ala Asp Gln Ala Ser Glu Asn
85 90 95

Val Glu Ala Tyr Arg Ser Glu Ile Asn Arg Ile Ala Gln Ala Lys Tyr
100 105 110

Arg Gly Thr Val Thr Asp Pro Leu Ser Ile Ala Val Ser Ala Glu Asp
115 120 125

Pro Gln Asn Val Ile Asp Arg Met Ser Tyr Leu Ser Thr Leu Thr Lys
130 135 140

Ser Thr Ser Asp Val Val Glu Ser Leu Asn Ala Glu Thr Glu Lys Ser
145 150 155 160

Ala Glu Ala Val Tyr Gln Ala Asn Arg Thr Lys Ala Glu Ala Glu Phe
165 170 175

Gln Leu Gly Gln Leu Lys Val Arg Gln Ala Glu Leu Glu Ser Glu Lys
180 185 190

Glu Ala Leu Asp Gly Arg Lys Ser Glu Ile Arg Asp Arg Val Asp Ala
195 200 205

Leu Thr Pro Gln Glu Arg Glu Met Trp Val Ala Lys Asn Gly Pro Leu
210 215 220

Asp Ile Asp Leu Thr Asp Leu Leu Gly Leu Ser Ala Ala Thr Ser Gly
225 230 235 240

Ala Val Asp Ala Ala Leu Ser Lys Leu Gly Ser Pro Tyr Gly Trp Gly
245 250 255

Gly Ile Gly Pro Asn Glu Phe Asp Cys Ser Gly Leu Ile Tyr Trp Ala
260 265 270

Tyr Gln Gln Met Gly Lys Thr Leu Pro Arg Thr Ser Gln Ala Gln Met
275 280 285

Ala Gly Gly Thr Pro Val Ser Arg Asp Glu Leu Gln Pro Gly Asp Val
290 295 300

Ile Gly Tyr Tyr Pro Gly Ala Thr His Val Gly Leu Tyr Ile Gly Asp
305 310 315 320

Gly Lys Ile Val His Ala Ser Asp Tyr Gly Ile Pro Val Gln Val Val
325 330 335

Ser Val Asp Ser Ala Pro Phe Tyr Gly Ala Arg Arg Tyr
340 345

<210> SEQ ID NO 3
<211> LENGTH: 209
<212> TYPE: PRT
<213> ORGANISM: Corynebacterium sp.
<220> FEATURE:
<221> NAME/KEY: PEPTIDE
<222> LOCATION: (1)...(209)
<223> OTHER INFORMATION: NCgl2108

<400> SEQUENCE: 3

Met Gly Lys His Arg Arg Asn Asn Ser Asn Ala Thr Arg Lys Ala Val
1 5 10 15

Ala Ala Ser Ala Val Ala Leu Gly Ala Thr Ala Ala Ile Ala Ser Pro
20 25 30

Ala Gln Ala Ala Glu Val Val Val Pro Gly Thr Gly Ile Ser Val Asp
35 40 45

Ile Ala Gly Ile Glu Thr Thr Pro Gly Leu Asn Asn Val Pro Gly Ile
50 55 60

-continued

```
Asp Gln Trp Ile Pro Ser Leu Ser Ser Gln Ala Ala Pro Thr Ala Tyr
65                  70                  75                  80

Ala Ala Val Ile Asp Ala Pro Ala Ala Gln Ala Ala Pro Ala Ala Ser
                85                  90                  95

Thr Gly Gln Ala Ile Val Asp Ala Ala Arg Thr Lys Ile Gly Ser Pro
            100                 105                 110

Tyr Gly Trp Gly Ala Thr Gly Pro Asn Ala Phe Asp Cys Ser Gly Leu
        115                 120                 125

Thr Ser Trp Ala Tyr Ser Gln Val Gly Lys Ser Ile Pro Arg Thr Ser
    130                 135                 140

Gln Ala Gln Ala Ala Gln Gly Thr Pro Val Ala Tyr Ser Asp Leu Gln
145                 150                 155                 160

Ala Gly Asp Ile Val Ala Phe Tyr Ser Gly Ala Thr His Val Gly Ile
                165                 170                 175

Tyr Ser Gly His Gly Thr Val Ile His Ala Leu Asn Ser Ser Thr Pro
            180                 185                 190

Leu Ser Glu His Ser Leu Asp Tyr Met Pro Phe His Ser Ala Val Arg
        195                 200                 205

Phe


<210> SEQ ID NO 4
<211> LENGTH: 414
<212> TYPE: PRT
<213> ORGANISM: Corynebacterium sp.
<220> FEATURE:
<221> NAME/KEY: PEPTIDE
<222> LOCATION: (1)...(414)
<223> OTHER INFORMATION: NCgl2986

<400> SEQUENCE: 4

Met Asp Glu Leu Tyr Pro Leu Ile Ile Leu Asn Met Asn Asp Gly Arg
1               5                   10                  15

Ser Arg Val Ser Lys Val Leu Arg Val Gly Asp Arg Ser Pro Arg Val
            20                  25                  30

Ala Glu Val Arg Thr Thr Leu Ala Arg Leu Gly Val Ile Glu Gly Tyr
        35                  40                  45

Ser Arg Glu Met Ser Ala Lys Thr Glu Ser Gln Lys Phe His Glu Glu
    50                  55                  60

Glu Thr Leu Phe Asp Glu Glu Leu Ser Leu Ser Ile Lys Ser Phe Gln
65                  70                  75                  80

Gln Ala Arg Gly Val Val Pro Ser Gly Leu Ile Asp Asp Pro Thr Leu
                85                  90                  95

Arg Ala Ile Arg Glu Ala Ser Tyr Thr Leu Gly Thr Arg Val Leu Ala
            100                 105                 110

Tyr Gln Pro Gly Asn Gln Leu Val Gly Asp Asp Val Val Glu Ile Gln
        115                 120                 125

Ser His Leu Gln Glu Leu Gly Phe Tyr Ala Asp Arg Val Asp Gly His
    130                 135                 140

Phe Gly Glu Leu Thr His Lys Ala Val Met Asn Tyr Gln Leu Asn Tyr
145                 150                 155                 160

Gly Met Gln Val Asp Gly Ile Cys Gly Pro Asp Thr Ile Arg Ala Leu
                165                 170                 175

Ser Arg Leu Gly Leu Arg Ile Lys Gly Gly Ser Ala Gln Ala Ile Arg
            180                 185                 190

Glu Arg Glu Arg Met Arg Asn Ala Gly Pro Arg Leu Ala Gly Lys Arg
```

-continued

```
        195                 200                 205

Val Val Ile Asp Pro Ala Leu Gly Gly Ser Asn Lys Gly Gln Ile Val
    210                 215                 220

Lys Gly Pro Tyr Gly Glu Ile Ser Glu Glu Glu Ile Leu Trp Asp Leu
225                 230                 235                 240

Ala Thr Arg Leu Glu Gly Arg Met Ile Ala Thr Gly Met Glu Thr Ile
                245                 250                 255

Leu Ser Arg Pro His Met Asp Asp Pro Ser Ser Arg Asp Arg Ala Ser
            260                 265                 270

Ile Ala Asn Ala Phe Gly Ala Asp Leu Met Leu Ser Leu His Cys Asp
        275                 280                 285

Ser Tyr Pro Asn Glu Lys Ala Asn Gly Val Ala Ser Phe Tyr Phe Gly
    290                 295                 300

Ser Glu Asn Gly Thr Asn Ser Leu Thr Gly Glu Thr Leu Ser Ala Tyr
305                 310                 315                 320

Ile Gln Lys Glu Ile Val Ala Arg Thr Pro Leu Asn Asn Cys Gly Ser
                325                 330                 335

His Ala Arg Thr Trp Asp Leu Leu Arg Leu Thr Arg Met Pro Met Val
            340                 345                 350

Glu Val Val Thr Gly Tyr Leu Thr Asn Pro Asp Asp Leu Ala Val Leu
        355                 360                 365

Thr Asp Pro Gln Met Arg Asp His Ile Ala Glu Ala Ile Val Val Ala
    370                 375                 380

Val Lys Arg Leu Tyr Leu Leu Asp Glu Glu Ala Gln Pro Lys Thr Gly
385                 390                 395                 400

Thr Phe Lys Phe Ser Glu Leu Leu Gln Ser Glu Gln Ala Gly
                405                 410


<210> SEQ ID NO 5
<211> LENGTH: 1815
<212> TYPE: DNA
<213> ORGANISM: Corynebacterium sp.
<220> FEATURE:
<221> NAME/KEY: gene
<222> LOCATION: (1)...(1815)

<400> SEQUENCE: 5

ttgaccaggg cgttgattgc gcttgcagta agcggagctt tgcttagttc catgactccg     60

gcggtggcgc agccacagaa tccggatgac gcagccattg cacaggcaga ggaaaatgtt    120

tcggcgggcg atggggaagt cgcccgcctg gcaggatctt tgtccagcac tgacgcggaa    180

attaaccgcg tcgagctgga aatgggtgct ctgcgtgaag aagtgaacaa gtccctcgtg    240

gatttgcatg atgcgcaggc aatcgccgag caggcccgcc aagatgcact tgcagccaag    300

aaggatctcg atgattctca agcgcagatc gaagcagccc aagagcgcct tgatgagatt    360

tcacgtgcag cgtatcgcca aaacggaacc tccaaggggc tttcaggcat ctcgggcaat    420

ggaaattctg aagatgcgct agatcgtcag acttacctgc gaaccagtgc ggaaaagcag    480

caggcagctg ttgaagagct tgatcgcctc cgtacggaaa acgccaacaa ggaatcggtg    540

ttgcgccagg cccgcatcgt tgctgagcag cgtgaggcgg aagccgtcga aaagcaagtc    600

cagaccgagg ctgcaattgc cgcaaacagc gagcagctca atgtcttgac taacaatcgc    660

agtaccttgg ttgcccagcg tgatggggct gagcgcaact tggccatcgc tcgtgcgcag    720

gcggataatc tgcaaggtca gcgtgctgag tacgaggaat tccagcaggc agagcaggct    780

cgcatccagg cggaagcgga agctcaggct gctgcggagg agaagcgtcg tgccgatgag    840
```

```
gctgctgcac aggcagccgc tgaagctcaa gaagctgccc agcaagctca ggcggcggag    900

gaagcccaag ccgcgcaagc agctgagaca gcacaagccc aagccgcgca agctgcggaa    960

acccaagctg cacaagccgc gcaagctcag gcagaagcga atgatcgtgc cgccgcgcaa   1020

cagcgtgctg cagaggctca agcagcagcg gaacaggcgc aacgtgaggc tgacgctcag   1080

gcggccaacg atgcccaagc tcaggcactg cgtgaacagg cgctcaccgc agcctccatc   1140

gctgcggctg ctctaattgc ggcgagccag tccagccatg ccactactca aaatccttac   1200

ccaactgatg aagacgcgga tccgaccgat attgcggaca tccaaggccc aacgcagcca   1260

ggtacgggtg agtctggaga ttcccagagc aactccagcg acaacgattc cacaggcaac   1320

gattccacag gctctgactc ttcagattca gattcctccg gcaacgattc ttcagaggtt   1380

atttccggcg atcgttccgc tcagattgag actgtgattg cgcgcgccat gagccagttg   1440

ggtgtgcagt acgcatgggg tggcggtaac gctaatggcc caactctggg tatccgtgac   1500

ggtggcgtgg cggactctta cggcgattac aacaaggttg gcttcgactg ctctggactg   1560

accttgtatg cgtttgcggg tgtgggaatt tcacttcctc actacacggg ctaccagtac   1620

cagcacggca ccaaggtgtc gccttctgag atgcaacgtg gcgatctgat cttctatggt   1680

ccgggagcgt ctcagcacgt ggcaatttac ctcggtgatg gtcagatgat tgaggctccg   1740

aattcgggtt ctgtcgtgaa gatttctcct gttcgctgga gcggaatgac cgagagcgtg   1800

gtacgcctca tttag                                                    1815
```

```
<210> SEQ ID NO 6
<211> LENGTH: 1050
<212> TYPE: DNA
<213> ORGANISM: Corynebacterium sp.
<220> FEATURE:
<221> NAME/KEY: gene
<222> LOCATION: (1)...(1050)
<223> OTHER INFORMATION: NCgl2107

<400> SEQUENCE: 6

ttgaatgagg ttgatagggg atttttgaag atgtttggtc gccgttgggt gagcgttgtg     60

gcgtcatgtg ttatcgcaag cacgctgatt ctggtgcctt cgcattccgg tgcggaggaa    120

gtcgatcaac tgattgctga tatcgagcat gtctctcagg aaacgtctgc ccagaatgag    180

gaagtcaaac agcttgagat tgatattgag gctcgtgagg tcacgatcaa ggaagttcag    240

gagcagtcgg taagctaccg tgaggcggct gatcaagcat cggagaatgt cgaagcttat    300

cgttcggaga tcaatcggat cgctcaggcg aagtatcgtg gcacagtcac ggatcctttg    360

agcattgcgg tgtctgcaga agatccacaa aacgtgattg atcggatgag ctacctttca    420

acgttgacta agtccactag tgatgtggtt gaatccctca acgcggagac tgagaagtcc    480

gcagaagctg tgtatcaagc aaaccgtact aaggcggaag cggagttcca gttggggcag    540

ctgaaggtac gccaggcgga gcttgaatct gaaaaggaag cattggatgg tcgaaaatcg    600

gagatccgag accgggtgga tgccctgacg ccacaggagc gggaaatgtg ggttgctaag    660

aatggtccat tggacattga tctgactgat ttgcttggtc tttccgctgc gacttcgggt    720

gcggtggatg ctgccttgtc taagttggga agcccttatg gttggggtgg cattggccca    780

aatgagtttg attgctcagg tttgatctat tgggcgtatc agcagatggg taagactttg    840

ccacgtacgt ctcaagctca gatggctggc ggaacgccgg tgagcagaga tgagctgcag    900

cctggcgatg tcattggata ttacccaggt gctactcacg tgggactgta tattggggac    960
```

-continued ggaaagattg tgcacgcctc agactacgga atccctgtgc aggtggtatc tgttgattca 1020
gcaccgtttt atggtgcgcg tcgctactaa 1050

<210> SEQ ID NO 7
<211> LENGTH: 630
<212> TYPE: DNA
<213> ORGANISM: Corynebacterium sp.
<220> FEATURE:
<221> NAME/KEY: gene
<222> LOCATION: (1)...(630)
<223> OTHER INFORMATION: NCgl2108

<400> SEQUENCE: 7
gtgggtaagc accgtcgcaa caattcaaac gcaactcgca aggctgtagc agcatctgca 60
gttgcgcttg gagcaaccgc agctatcgcc tccccagcac aggcagctga ggttgttgtt 120
cctggcaccg gaatcagcgt tgacatcgct ggcatcgaga ccactccagg tcttaacaac 180
gttccaggaa tcgatcagtg gatcccttcc cttagcagcc aggcagctcc tactgcttac 240
gcagccgtca ttgatgcacc tgcagcacag gctgcacctg cagcaagcac cggtcaggca 300
atcgttgatg cagcgcgcac caagattggt tccccatacg gttggggtgc taccggtcct 360
aacgctttcg actgctccgg ccttacctca tgggcataca gccaggttgg caagtccatc 420
ccacgtacct cccaggctca ggctgcacag ggcacccctg ttgcttactc tgaccttcag 480
gctggcgaca tcgttgcgtt ctactccggc gctacccacg ttggtatcta ctccggccac 540
ggcaccgtta tccacgcact gaacagcagc accccctctgt ctgagcactc cttggattac 600
atgccattcc actctgcagt tcgtttctaa 630

<210> SEQ ID NO 8
<211> LENGTH: 1245
<212> TYPE: DNA
<213> ORGANISM: Corynebacterium sp.
<220> FEATURE:
<221> NAME/KEY: gene
<222> LOCATION: (1)...(1245)
<223> OTHER INFORMATION: NCgl2986

<400> SEQUENCE: 8
gtggatgaac tatatccatt gataattttg aacatgaatg atggaaggag cagggtgtct 60
aaagtcctga gagttggcga tcgcagcccg cgcgtggcag aagtgcgcac tacgctcgct 120
cgcctcggtg tgattgaagg ctattccagg gagatgtctg caaagacaga atcccagaag 180
ttccacgaag aagagacgct tttcgacgaa gaactcagcc tcagcatcaa gtcattccag 240
caagctcgag gagtcgttcc ctccgggctt attgacgacc ccaccctgcg cgcaatccgc 300
gaagcctcct acaccctggg aacccgcgtg ctggcctacc agcccggcaa ccagcttgtt 360
ggtgacgacg ttgtagaaat ccaatcccat ctccaagagc tcggcttcta cgccgaccgt 420
gtggatggac attttggcga gctcacacac aaagctgtga tgaactacca actcaactac 480
ggcatgcagg tagacggcat ctgtggccct gacaccatcc gtgcgctgtc ccgacttggt 540
ctgcgcatca agggtggctc tgctcaagct atccgtgaac gcgaacgcat gcgcaatgca 600
ggcccacgtc ttgctggcaa gcgtgtggtc attgatcctg cgcttggggg ctccaacaag 660
ggtcagatcg tgaaaggccc ctacggtgag atctctgagg aagaaatcct ctgggatttg 720
gccacccgcc tggaaggtcg catgatcgca acaggcatgg aaaccattct gtcgcgcccg 780
cacatggatg atcccagcag ccgtgatcgc gcgtcgatcg cgaatgcttt cggcgctgac 840
ctcatgctga gcctgcactg cgattcctac ccgaatgaaa aagctaacgg cgtggccagc 900

-continued

```
ttctacttcg gttcggaaaa cggcaccaac tccttgaccg gtgaaacgct ctccgcgtac     960

atccaaaaag agatcgttgc ccgcacccca ctgaacaact gtggcagcca tgcccgtacc    1020

tgggatctgc tgcgcctcac gcgcatgccc atggtggaag ttgtcaccgg ttacctcacc    1080

aaccccgatg acctggcagt tctgactgat ccacaaatgc gtgatcacat tgccgaagcc    1140

atcgttgtcg ccgtcaagcg cctgtacctc cttgatgagg aagcacagcc caagaccgga    1200

accttcaagt tctctgagct gttgcaatca gagcaggctg gctaa                    1245


<210> SEQ ID NO 9
<211> LENGTH: 25
<212> TYPE: DNA
<213> ORGANISM: Artificial Sequence
<220> FEATURE:
<223> OTHER INFORMATION: Kit primer

<400> SEQUENCE: 9

acctacaaca aagctctcat caacc                                            25


<210> SEQ ID NO 10
<211> LENGTH: 24
<212> TYPE: DNA
<213> ORGANISM: Artificial Sequence
<220> FEATURE:
<223> OTHER INFORMATION: Kit primer

<400> SEQUENCE: 10

ctaccctgtg gaacacctac atct                                             24


<210> SEQ ID NO 11
<211> LENGTH: 34
<212> TYPE: DNA
<213> ORGANISM: Artificial Sequence
<220> FEATURE:
<223> OTHER INFORMATION: NCgl1480 primer

<400> SEQUENCE: 11

ccggggatcc tctagaacct tgaaacttcc actc                                  34


<210> SEQ ID NO 12
<211> LENGTH: 36
<212> TYPE: DNA
<213> ORGANISM: Artificial Sequence
<220> FEATURE:
<223> OTHER INFORMATION: NCgl1480 primer

<400> SEQUENCE: 12

ctcctgacga actatttcaa atcccctatc aacctc                                36


<210> SEQ ID NO 13
<211> LENGTH: 36
<212> TYPE: DNA
<213> ORGANISM: Artificial Sequence
<220> FEATURE:
<223> OTHER INFORMATION: NCgl1480 primer

<400> SEQUENCE: 13

caccgaggta aattgccatg caagcgcaat caacgc                                36


<210> SEQ ID NO 14
<211> LENGTH: 34
<212> TYPE: DNA
<213> ORGANISM: Artificial Sequence
<220> FEATURE:
```

<223> OTHER INFORMATION: NCgl1480 primer

<400> SEQUENCE: 14
gcaggtcgac tctagaaacc acacattatc gatc 34

<210> SEQ ID NO 15
<211> LENGTH: 35
<212> TYPE: DNA
<213> ORGANISM: Artificial Sequence
<220> FEATURE:
<223> OTHER INFORMATION: NCgl2107 primer

<400> SEQUENCE: 15
ccggggatcc tctagagcac agggcacccc tgttg 35

<210> SEQ ID NO 16
<211> LENGTH: 36
<212> TYPE: DNA
<213> ORGANISM: Artificial Sequence
<220> FEATURE:
<223> OTHER INFORMATION: NCgl2107 primer

<400> SEQUENCE: 16
ctcctgacga actatttcaa atcccctatc aacctc 36

<210> SEQ ID NO 17
<211> LENGTH: 36
<212> TYPE: DNA
<213> ORGANISM: Artificial Sequence
<220> FEATURE:
<223> OTHER INFORMATION: NCgl2107 primer

<400> SEQUENCE: 17
gaggttgata ggggatttga aatagttcgt caggag 36

<210> SEQ ID NO 18
<211> LENGTH: 34
<212> TYPE: DNA
<213> ORGANISM: Artificial Sequence
<220> FEATURE:
<223> OTHER INFORMATION: NCgl2107 primer

<400> SEQUENCE: 18
gcaggtcgac tctagaaacc acacattatc gatc 34

<210> SEQ ID NO 19
<211> LENGTH: 34
<212> TYPE: DNA
<213> ORGANISM: Artificial Sequence
<220> FEATURE:
<223> OTHER INFORMATION: NCgl2108 primer

<400> SEQUENCE: 19
ccggggatcc tctagagaac ccttagtagt tggg 34

<210> SEQ ID NO 20
<211> LENGTH: 36
<212> TYPE: DNA
<213> ORGANISM: Artificial Sequence
<220> FEATURE:
<223> OTHER INFORMATION: NCgl2108 primer

<400> SEQUENCE: 20
gtaatccaag gagtgctcac ccactgatga aactcc 36

-continued

<210> SEQ ID NO 21
<211> LENGTH: 36
<212> TYPE: DNA
<213> ORGANISM: Artificial Sequence
<220> FEATURE:
<223> OTHER INFORMATION: NCgl2108 primer

<400> SEQUENCE: 21
ggagtttcat cagtgggtga gcactccttg gattac 36

<210> SEQ ID NO 22
<211> LENGTH: 34
<212> TYPE: DNA
<213> ORGANISM: Artificial Sequence
<220> FEATURE:
<223> OTHER INFORMATION: NCgl2108 primer

<400> SEQUENCE: 22
gcaggtcgac tctagacgag cctcaatatc aatc 34

<210> SEQ ID NO 23
<211> LENGTH: 34
<212> TYPE: DNA
<213> ORGANISM: Artificial Sequence
<220> FEATURE:
<223> OTHER INFORMATION: NCgl2986 primer

<400> SEQUENCE: 23
ccggggatcc tctagattag gagaaaccat gagc 34

<210> SEQ ID NO 24
<211> LENGTH: 36
<212> TYPE: DNA
<213> ORGANISM: Artificial Sequence
<220> FEATURE:
<223> OTHER INFORMATION: NCgl2986 primer

<400> SEQUENCE: 24
atcagtcaga actgccagga ctgcagtaag aatacc 36

<210> SEQ ID NO 25
<211> LENGTH: 36
<212> TYPE: DNA
<213> ORGANISM: Artificial Sequence
<220> FEATURE:
<223> OTHER INFORMATION: NCgl2986 primer

<400> SEQUENCE: 25
ggtattctta ctgcagtcct ggcagttctg actgat 36

<210> SEQ ID NO 26
<211> LENGTH: 34
<212> TYPE: DNA
<213> ORGANISM: Artificial Sequence
<220> FEATURE:
<223> OTHER INFORMATION: NCgl2986 primer

<400> SEQUENCE: 26
gcaggtcgac tctagagttg aggcgtttgg atac 34

MICROORGANISM PRODUCING L-LYSINE AND METHOD FOR PRODUCING L-LYSINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_434USPC_SEQUENCE_LISTING.txt. The text file is 22.3 KB, was created on Dec. 27, 2017, and is being submitted electronically via EFS-Web.

TECHNICAL FIELD

The present disclosure relates to a microorganism producing L-lysine and a method for producing L-lysine using the same.

BACKGROUND ART

L-Amino acids, in particular L-lysine, which are used in animal feeds, therapeutic agents for humans, or the cosmetics industry are mainly produced through fermentation using a strain of the genus *Corynebacterium* or a strain of the genus *Escherichia*. Accordingly, various studies are underway to develop strains producing L-lysine in high yield and fermentation technology thereof. However, research on the control of cell lysis, which may cause decreased productivity in later stages of fermentation, is still insufficient.

Meanwhile, cell wall hydrolases are known as enzymes that degrade bacterial cell walls, and are present in all microorganisms having peptidoglycan (Rice K C & Bayles K W. Microbiol Mol Biol Rev. 2008. 72:85-109). Although research on such cell wall hydrolases has been conducted in various bacteria, their precise control mechanism is still unknown.

A model for the cell lysis mechanism occurring during the cultivation of microorganisms has recently been proposed in pneumococcus (Mellroth P et al. J Biol Chem. 2012. 287: 11018-29). Specifically, when cells are exposed to various types of stresses, an activity of cell wall hydrolase present on the outer wall of the cells increases, thereby initiating cell wall decomposition. When the cells are dissolved by the continuous action of such cell wall hydrolase, the cell wall hydrolase present in the cytoplasm is exposed to the outside of the cells. It has been reported that the surrounding cells are dissolved when a series of processes occurs continuously so that the amount of the cell wall hydrolase exceeds a threshold outside the cells. However, a correlation between cell lysis generated during the fermentation culture process and amino acid production is still unknown.

DISCLOSURE

Technical Problem

The present inventors have made efforts to continuously search for an effective trait capable of increasing L-lysine productivity in a microorganism of the genus *Corynebacterium*, which is a representative L-lysine-producing strain. As a result, the present inventors have confirmed that the L-lysine productivity increased when a gene encoding a protein involved in cell wall hydrolysis was deficient, and that the increase in the lysine productivity was affected when an additional gene encoding a protein having a similar function was deficient, thereby completing the present disclosure.

Technical Solution

An object of the present disclosure is to provide a microorganism of the genus *Corynebacterium* producing L-lysine.

Another object of the present disclosure is to provide a method for preparing L-lysine using the microorganism of the genus *Corynebacterium*, which produces L-lysine.

Advantageous Effects

The microorganism according to the present disclosure is a microorganism of the genus *Corynebacterium*, which is modified such that an activity of a protein involved in cell wall hydrolysis is reduced or inactivated in comparison with an endogenous activity thereof. That is, the microorganism according to the present disclosure is a new strain which leads to an increase in the productivity in a later stage of fermentation, and thus is applied as a novel paradigm of the microorganism of the genus *Corynebacterium*, which produces L-lysine, thereby providing a microorganism capable of producing L-lysine in high yield. Accordingly, the prepared L-lysine can be applied not only to animal feeds or animal feed additives but also to various products such as human foods, food additives, medicines, etc.

BEST MODE

In order to achieve the above objects, an aspect of the present disclosure provides a microorganism of the genus *Corynebacterium* producing L-lysine, which is modified such that an activity of a protein involved in cell wall hydrolysis is inactivated in comparison with an endogenous activity thereof.

As used herein, the term “protein involved in cell wall hydrolysis” refers to a relevant protein capable of hydrolyzing a cell wall in a microorganism of the genus *Corynebacterium*. The protein involved in cell wall hydrolysis may be a cell wall-associated hydrolase or an N-acetylmuramoyl-L-alanine amidase, but is not limited thereto.

As described above, as long as a protein has an activity of a relevant protein capable of hydrolyzing a cell wall in the microorganism, the protein and gene sequences can be obtained from a known database. In addition, Genbank of NCBI, etc. may be used as examples of the known database, but these are not limited thereto.

The cell wall-associated hydrolase may be an NCgl1480 gene-encoding protein, NCgl2107 gene-encoding protein, or NCgl2108 gene-encoding protein derived from a microorganism of the genus *Corynebacterium*, specifically from *Corynebacterium glutamicum*, but is not limited thereto. As a specific example, the cell wall-associated hydrolase may have the amino acid of SEQ ID NOS: 1, 2, or 3, but may include the protein sequence having the activity above without limitation. In addition, any nucleotide sequences may be included therein without limitation as long as it is a nucleotide sequence encoding a protein having the activity of the cell wall-associated hydrolase. As a specific example, it may be a protein encoded by the nucleotide sequence of SEQ ID NOS: 5, 6, or 7, but is not limited thereto.

The N-acetylmuramoyl-L-alanine amidase may be an NCgl2986 gene-encoding protein derived from a microorganism of the genus *Corynebacterium*, specifically from *Corynebacterium glutamicum*. Specifically, the N-acetylmuramoyl-L-alanine amidase may have the amino acid sequence of SEQ ID NO: 4, but any amino acid sequences of the protein having the activity above may be included without limitation. In addition, any nucleotide sequence may be included without limitation as long as the nucleotide sequence encodes a protein having the activity of the N-acetylmuramoyl-L-alanine amidase. For example, it may be a protein encoded by the nucleotide sequence of SEQ ID NO: 8, but is not limited thereto.

Each of the proteins described above may include without limitation, in addition to the amino acid sequences represented by SEQ ID NOS, any amino acid sequence which has a homology to the above-listed amino acid sequences of 80% or higher, preferably 90% or higher, more preferably 95% or higher, and even more preferably 97% or higher, as long as the amino acid sequences encode proteins which have an effect substantially the same as or corresponding to each of the proteins. Additionally, it is obvious that any modified protein having the homology described above can belong to the scope of the present disclosure, although the protein may have an amino acid sequence with a partial deletion, modification, substitution, or addition therein.

Additionally, the genes encoding each of the proteins of the present disclosure may also include without limitation, in addition to the nucleotide sequences described by SEQ ID NOS, any gene sequence encoding the proteins which has homology to each of the above-listed nucleotide sequences of 80% or higher, preferably 90% or higher, more preferably 95% or higher, even more preferably 98% or higher, and most preferably 99% or higher, as long as the gene sequences encodes a protein which has an effect substantially the same as or corresponding to each of the proteins. Additionally, it is obvious that any nucleotide sequence having the above homologies can belong to the scope of the present disclosure, although the sequence may have a partial deletion, modification, substitution, or addition therein.

As used herein, "homology" refers to the similarity in nucleotide sequences or amino acid sequences of gene coding for a protein. When homology is sufficiently high, products of the corresponding gene may be the same or have a similar activity. That is, it refers to a percentage of identity between two polynucleotide or polypeptide moieties. Sequence correspondence from one moiety to another may be determined by a technique known in the art. For example, homology may be determined by aligning the sequence information of two polynucleotide molecules or two polypeptide molecules directly by using a computer program that is readily available and capable of aligning sequence information. The computer program may be BLAST (NCBI), CLC Main Workbench (CLC bio), MegAlign™ (DNASTAR Inc), etc. In addition, homology may be determined by hybridizing the polynucleotides under the condition for forming a stable double-strand in the homologous regions and then digesting the hybridized strand by a single-strand-specific nuclease to determine a size of a digested fragment.

As used herein, the term "endogenous activity" refers to a protein activity in the state before a microorganism modification or in its native state.

As used herein, the term "activity of an enzyme modified to be inactivated in comparison with its endogenous activity" refers to an activity where a gene encoding an enzyme is not expressed at all compared to a wild-type strain or a strain before a modification, or refers to a reduction or elimination of an activity even when the gene is expressed.

The "inactivation of an activity compared to its endogenous activity" refers to a reduction or elimination of the activity when compared with that possessed in its natural state or the state before a modification. The reduction is a concept referring to a case when the activity of an enzyme is reduced compared with that originally possessed by the microorganism due to a modification in the enzyme-encoding gene, a case when the level of overall enzyme expression is lower than that of the natural type strain of the microorganism or the strain before a modification, or a combination thereof.

The "elimination of an activity" refers to a case when a gene encoding an enzyme is not expressed at all compared to that of the natural type strain or the strain before a modification, and/or refers to a case when the gene is expressed but exhibits no activity.

The method of a modification to inactivate the enzyme activity can be achieved by application of various methods well known in the art. Examples of the methods may include a method of replacing the gene encoding the enzyme on the chromosome with a mutated gene so that the enzyme activity can be reduced, including the case when the enzyme activity is removed; a method of introducing a modification on the expression-regulating sequence of the gene encoding the enzyme on the chromosome; a method of replacing the expression-regulating sequence of the gene encoding the enzyme with a sequence having a weak activity or no activity; a method of deleting a part of or the entire gene encoding the enzyme on the chromosome; a method of introducing an antisense oligonucleotide (e.g., antisense RNA), which inhibits the translation from the mRNA into an enzyme via a complementary binding to the transcript of the gene on the chromosome; a method of making the attachment of ribosome impossible by forming a secondary structure by artificially adding a Shine-Dalgarno (SD) sequence and its complementary sequence on the front end of the SD sequence of the gene encoding the enzyme; a method of reverse transcription engineering (RTE), which adds a promoter so as to be reversely transcribed on the 3' terminus of the open reading frame (ORF) of the corresponding sequence, etc., and also include a combination thereof, but are not limited thereto.

Specifically, the method of deleting a part of or the entire gene encoding an enzyme may be performed by replacing the polynucleotide, which encodes the endogenous target protein within the chromosome via a vector for inserting chromosome into a microorganism, with a polynucleotide or a marker where part of the nucleic acid sequence is deleted. For example, a method of gene deletion via homologous recombination may be used.

As used herein, the term "part", although it may vary depending on the kinds of polynucleotide, may specifically refer to 1 nucleotide to 300 nucleotides, more specifically 1 nucleotide to 100 nucleotides, and even more specifically 1 nucleotide to 50 nucleotides, but is not limited thereto.

As used herein, the term "homologous recombination" refers to genetic recombination that occurs via crossover at a locus of a gene chain having a mutual homology.

According to an exemplary embodiment of the present disclosure, the proteins were inactivated by homologous recombination.

Specifically, the method of modifying an expression regulatory sequence may be carried out by inducing a modification on the expression regulatory sequence through deletion, insertion, non-conservative or conservative substitution of a nucleic acid sequence of the expression regulatory sequence, or a combination thereof; or may be carried out by replacing the sequence with a weaker promoter. The expression regulatory sequence includes a promoter, an operator sequence, a sequence encoding a ribosome-binding site, and a sequence for regulating the termination of transcription and translation.

Additionally, the method of modifying a gene sequence on the chromosome may be carried out by inducing a modification in the sequence by deletion, insertion, non-conservative or conservative substitution of the gene sequence, or a combination thereof so as to further reduce the enzyme activity; or by replacing the sequence with a gene sequence improved to have an additional weaker activity or with a gene sequence improved to have no activity.

As used herein, the term "microorganism producing L-lysine" refers to a microorganism strain capable of producing L-lysine by fermentation. For example, it includes a strain capable of increasing L-lysine productivity by modifying the sequence via the manipulation of the present disclosure such that an activity of a protein involved in cell wall hydrolysis is inactivated in comparison with its endogenous activity; and by regulating cell lysis for the production of lysine, which occurs during fermentation, but is not limited thereto.

In the present disclosure, the microorganism producing L-lysine may include all microorganisms of the genus *Corynebacterium*, which is capable of being modified such that an activity of a protein involved in cell wall hydrolysis is inactivated in comparison with its endogenous activity. For example, *Corynebacterium glutamicum, Corynebacterium ammoniagenes, Corynebacterium thermoaminogenes, Brevibacterium flavum*, or *Brevibacterium fermentum* may be used, but the microorganism is not limited thereto. For example, *Corynebacterium glutamicum* may be used for the microorganism of the genus *Corynebacterium*. The modified microorganism of the genus *Corynebacterium* is characterized in that L-lysine productivity is enhanced compared to a microorganism which is not modified such that an activity of a protein involved in cell wall hydrolysis is inactivated in comparison with its endogenous activity.

Another aspect of the present disclosure provides a method for preparing L-lysine, including: (i) culturing the microorganism of the genus *Corynebacterium*, which is modified such that an activity of a protein involved in cell wall hydrolysis is inactivated in comparison with its endogenous activity; and (ii) recovering L-lysine from the culture medium or the microorganism.

The microorganism of the genus *Corynebacterium*, in which L-lysine productivity is increased, is as described above.

As used herein, the term "culture" refers to culturing of a microorganism under artificially controlled environmental conditions. In the present disclosure, the method of culturing L-lysine using the microorganism of the genus *Corynebacterium* may be conducted using a method widely known in the art. Specifically, examples of the culture include a batch process and a fed batch or repeated fed batch process in a continuous manner, but are not limited thereto.

The medium used for the culturing should satisfy the requirements for a specific strain in an appropriate manner (for example, Manual of Methods for General Bacteriology. American Society for Bacteriology. Washington D.C., USA, 1981). Carbon sources that may be used in the present disclosure may include sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as gluconic acid, acetic acid, and pyruvic acid, but these are not limited thereto. These substances may be used alone or in a mixture. Nitrogen sources that may be used in the present disclosure may include peptone, yeast extract, meat extract, malt extract, corn steep liquor, defatted soybean cake, and urea or inorganic compounds, such as ammonium sulfate, ammonium chloride, ammonium phosphate, ammonium carbonate, and ammonium nitrate, but these are not limited thereto. These nitrogen sources may also be used alone or in a mixture. Phosphorus sources that may be used in the present disclosure may include potassium dihydrogen phosphate or dipotassium hydrogen phosphate, or corresponding sodium-containing salts, but these are not limited thereto. In addition, the culture medium may contain a metal salt such as magnesium sulfate or iron sulfate, which is required for the growth. Lastly, in addition to the above-described substances, essential growth factors such as amino acids and vitamins may be used. Additionally, suitable precursors may be used in the culture medium. These substances may be added to the medium during culturing in a batch or continuous manner. Such a variety of culture methods is disclosed, for example, in the literature ("Biochemical Engineering" by James M. Lee, Prentice-Hall International Editions, pp 138-176).

Basic compounds such as sodium hydroxide, potassium hydroxide, or ammonia, or acidic compounds such as phosphoric acid or sulfuric acid may be added to the culture medium in a suitable manner to adjust the pH of the culture medium. In addition, an anti-foaming agent such as fatty acid polyglycol ester may be used to suppress the formation of bubbles. In order to maintain the culture medium in an aerobic state, oxygen or oxygen-containing gas (e.g., air) may be injected into the culture medium. The temperature of the culture medium may be usually 20° C. to 45° C., preferably 25° C. to 40° C., but may be changed depending on conditions. The culture may be continued until the maximum amount of a desired L-amino acid is produced, and it may generally be achieved within 10 hours to 160 hours. L-Lysine may be released into the culture medium or contained in cells.

The method of the present disclosure for producing L-lysine may include a step of recovering lysine from the microorganism or the medium. Methods known in the art, such as centrifugation, filtration, anion-exchange chromatography, crystallization, HPLC, etc., may be used for the method for recovering L-lysine from the microorganism or the culture, but the method is not limited thereto.

The step of recovering may include a purification process.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation of Random Mutant Library Using Transposon

In order to obtain genes increasing lysine productivity, a vector library was prepared by the following method. The plasmid obtained using EZ-Tn5™<R6Kγori/KAN-2>Tnp Transposome™ Kit (Epicentre) was transformed using the strain KCCM11016P (the microorganism had been designated as KFCC10881 and re-deposited with the international depository institution under the Budapest Treaty, and was then designated the deposit accession number of KCCM11016P; Korean Patent No. 10-0159812) as a parent strain, and then spread on a complex medium plate containing kanamycin (25 mg/L) to obtain about 20,000 colonies.

<Complex Medium Plate (pH 7.0)>

10 g of glucose, 10 g of peptone, 5 g of beef extract, 5 g of yeast extract, 18.5 g of Brain Heart Infusion, 2.5 g of NaCl, 2 g of urea, 91 g of sorbitol, 20 g of agar (based on 1 L of distilled water)

Example 2: Screening of Random Mutant Library Using Transposon

Each of about 20,000 colonies obtained in Example 1 was inoculated into a selection medium (300 μL), and cultured in 96 deep well plates at 32° C. at 1000 rpm for about 24 hours. A ninhydrin method was used to analyze the amount of L-lysine produced in the culture medium (Moore, S., Stein, W. H., Photometric ninhydrin method for use in the chromatography of amino acids. J. Biol. Chem. 1948, 176, 367-388). Upon completion of the cultivation, the culture supernatant (10 μL) and ninhydrin reaction solution (190 μL) were reacted at 65° C. for 30 minutes. Thereafter, the absorbance was measured at a wavelength of 570 nm using a spectrophotometer, and about 60 kinds of colonies were selected as modified strains showing high absorbance as compared with the control, KCCM11016P. Other colonies showed similar or decreased absorbance compared to that of the control, the KCCM11016P strain.

60 kinds of the selected strains were cultured in the same manner as above, and the ninhydrin reaction was repeatedly performed. As a result, the top 10 strains having improved L-lysine productivity compared to the strain KCCM11016P were selected.

<Selection Medium (pH 8.0)>

10 g of glucose, 5.5 g of ammonium sulfate, 1.2 g of $MgSO_4$ $7H_2O$, 0.8 g of $KH_2PO_4$, 16.4 g of $K_2HPO_4$, 100 μg of biotin, 1000 μg of thiamine HCl, 2000 μg of calcium pantothenate, 2000 μg of nicotinamide (based on 1 L of distilled water)

Example 3: Analysis of L-Lysine Productivity of Selected Random Mutant Strains In order to finally select strains having increased L-lysine productivity, a reproducibility test was carried out in a flask using the medium below for 10 kinds of the strains selected in Example 2. 10 kinds of the strains and the control were inoculated in a corner-baffled flask (250 mL) containing the seed medium below (25 mL), and cultured while shaking at 30° C. and 200 rpm for 20 hours. The seed medium and production medium have the following compositions. Upon completion of the cultivation, L-lysine concentrations in the culture solution were analyzed using HPLC, and the L-lysine concentrations of each of the mutant strains are shown in Table 1 below.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4.7H_2O$, 100 μg of biotin, 1000 μg of thiamine HCl, 2000 μg of calcium pantothenate, 2000 μg of nicotinamide (based on 1 L of distilled water)

<Production Medium (pH 7.0)>

100 g of glucose, 40 g of $(NH_4)_2SO_4$, 2.5 g of soy bean protein, 5 g of corn steep solid, 3 g of urea, 1 g of $KH_2PO_4$, 0.5 g of $MgSO_4.7H_2O$, 100 μg of biotin, 1000 μg of thiamine HCl, 2000 μg of calcium pantothenate, 3000 μg of nicotinamide, 30 g of $CaCO_3$ (based on 1 L of distilled water)

TABLE 1

L-Lysine concentration of 10 selected mutant strains

| | | L-Lysine (g/L) | | | |
|---|---|---|---|---|---|
| | Strain | Batch 1 | Batch 2 | Batch 3 | Average |
| Control | KCCM11016P | 42.5 | 42.8 | 42.7 | 42.7 |
| 1 | KCCM11016P/mt-1 | 48.8 | 48.9 | 48.5 | 48.7 |
| 2 | KCCM11016P/mt-2 | 43.0 | 43.1 | 43.4 | 43.2 |
| 3 | KCCM11016P/mt-3 | 42.7 | 43.1 | 42.9 | 42.9 |
| 4 | KCCM11016P/mt-4 | 44.9 | 45.1 | 45.3 | 45.1 |
| 5 | KCCM11016P/mt-5 | 44.3 | 44.1 | 44.0 | 44.1 |
| 6 | KCCM11016P/mt-6 | 42.4 | 42.9 | 42.8 | 42.7 |
| 7 | KCCM11016P/mt-7 | 43.8 | 43.2 | 43.7 | 43.6 |
| 8 | KCCM11016P/mt-8 | 47.2 | 46.9 | 47.1 | 47.1 |
| 9 | KCCM11016P/mt-9 | 44.1 | 44.4 | 44.2 | 44.2 |
| 10 | KCCM11016P/mt-10 | 43.1 | 43.7 | 43.2 | 43.3 |

Among the 10 selected mutants above, KCCM11016P/mt-1 and KCCM11016P/mt-8 were finally selected as strains having significantly improved L-lysine productivity.

Example 4: Confirmation of Genes Involved in L-Lysine Productivity in Finally-Selected Strains and Selection of Additional Candidate Genes In this Example, identification of genes which are deficient due to random insertion of a transposon was attempted from the strains finally selected in Example 3. Genomic DNAs of KCCM11016P/mt-1 and KCCM11016P/mt-8 were extracted and then digested. Thereafter, the resultants were ligated, transformed into *E. coli* DH5a, and then plated on an LB solid medium containing kanamycin (25 mg/L). After selecting 20 kinds of the transformed colonies, plasmids containing parts of the unknown genes were obtained, and nucleotide sequences were analyzed using the sequences of SEQ ID NO: 9 and SEQ ID NO: 10 in the EZ-Tn5™ <R6Kγori/KAN-2>Tnp Transposome™ Kit (Table 2). As a result, it was confirmed that each of NCgl2108 and NCgl2986 genes was inactivated in the mutant strains.

TABLE 2

| | Sequence | SEQ ID NO |
|---|---|---|
| Kit primer | ACCTACAACAAAGCTCTCATCAACC | 9 |
| Kit primer | CTACCCTGTGGAACACCTACATCT | 10 |

The NCgl2108 and NCgl2986 genes identified as being deficient in the mutant strains selected in Example 3 were endogenously present in *Corynebacterium*, and thus identified as proteins involved in cell wall hydrolysis.

Based on the results of selecting 2 kinds of proteins involved in cell wall hydrolysis in random mutant strains using transposons, it was considered that deficiency in genes involved in cell wall hydrolysis would be effective in increasing L-lysine productivity. Accordingly, a search was conducted in the National Center for Biotechnology Information (NCBI) for genes involved in cell wall hydrolysis other than the NCgl2108 and NCgl2986 genes.

As a result of the search, NCgl1480 and NCgl2107 genes, which are endogenously present in *Corynebacterium*, were additionally selected as proteins involved in cell wall hydrolysis. Accordingly, in order to confirm whether deletion of the NCgl1480 and NCgl2107 genes affects L-lysine productivity, these genes were selected as additional deletion candidate genes.

Example 5: Production of Recombinant Plasmids for Inactivation of NCgl1480, NCgl2107, NCgl2108, and NCgl2986 Genes In this Example, in order to confirm whether inactivation of the NCgl1480, NCgl2107, NCgl2108, and NCgl2986 genes would affect L-lysine production, recombinant plasmids for deletion of the NCgl1480, NCgl2107, NCgl2108, and NCgl2986 genes selected in Example 4 on the chromosomes of the L-lysine-producing strains in *Corynebacterium* were produced.

Based on the nucleotide sequences reported in the U.S. National Institutes of Health GenBank (NIH Genbank), amino acid sequences of SEQ ID NOS: 1, 2, 3, and 4 of NCgl1480, NCgl2107, NCgl2108, and NCgl2986, as well as nucleotide sequences of SEQ ID NOS: 5, 6, 7, and 8 encoding the same, were obtained. In order to produce gene fragments, in which the open reading frame of each of NCgl1480, NCgl2107, NCgl2108, and NCgl2986 are internally deleted, the primers of SEQ ID NOS: 11 to 14 for NCgl1480, 15 to 18 for NCgl2107, 19 to 22 for NCgl2108, and 23 to 26 for NCgl2986 were produced based on the above SEQ ID NOS: 5, 6, 7, and 8. The sequences thereof are shown in Table 3 below.

TABLE 3

| Primer | Sequence | SEQ ID NO |
|---|---|---|
| NCgl1480 primer | CCGGGGATCCTCTAGAACCTTGAAACTTCCACTC | 11 |
| NCgl1480 primer | CTCCTGACGAACTATTTCAAATCCCCTATCAACCTC | 12 |
| NCgl1480 primer | CACCGAGGTAAATTGCCATGCAAGCGCAATCAACGC | 13 |
| NCgl1480 primer | GCAGGTCGACTCTAGAAACCACACATTATCGATC | 14 |
| NCgl2107 primer | CCGGGGATCCTCTAGAGCACAGGGCACCCCTGTTG | 15 |
| NCgl2107 primer | CTCCTGACGAACTATTTCAAATCCCCTATCAACCTC | 16 |
| NCgl2107 primer | GAGGTTGATAGGGGATTTGAAATAGTTCGTCAGGAG | 17 |
| NCgl2107 primer | GCAGGTCGACTCTAGAAACCACACATTATCGATC | 18 |
| NCgl2108 primer | CCGGGGATCCTCTAGAGAACCCTTAGTAGTTGGG | 19 |
| NCgl2108 primer | GTAATCCAAGGAGTGCTCACCCACTGATGAAACTCC | 20 |
| NCgl2108 primer | GGAGTTTCATCAGTGGGTGAGCACTCCTTGGATTAC | 21 |
| NCgl2108 primer | GCAGGTCGACTCTAGACGAGCCTCAATATCAATC | 22 |
| NCgl2986 primer | CCGGGGATCCTCTAGATTAGGAGAAACCATGAGC | 23 |
| NCgl2986 primer | ATCAGTCAGAACTGCCAGGACTGCAGTAAGAATACC | 24 |

TABLE 3-continued

| Primer | Sequence | SEQ ID NO |
|---|---|---|
| NCgl2986 primer | GGTATTCTTACTGCAGTCCTGGCAGTTCTGACTGAT | 25 |
| NCgl2986 primer | GCAGGTCGACTCTAGAGTTGAGGCGTTTGGATAC | 26 |

PCR was performed using the genomic DNA of *Corynebacterium glutamicum* ATCC13032 as a template along with nucleotide sequence pairs of SEQ ID NOS: 11 and 12, 13 and 14, 15 and 16, 17 and 18, 19 and 20, 21 and 22, 23 and 24, and 25 and 26, as primers (Sambrook et al., Molecular Cloning, a Laboratory Manual (1989), Cold Spring Harbor Laboratories). The PCR was performed under the following conditions: 30 cycles, each consisting of denaturation at 95° C. for 30 seconds, annealing at 50° C. for 30 seconds, and elongation at 72° C. for 1 minute.

As a result, two pairs of DNA fragments of 319 bp and 410 bp (NCgl1480-A and NCgl1480-B, respectively) containing upstream and downstream regions of the NCgl1480 gene; two pairs of DNA fragments of 324 bp and 300 bp (NCgl2107-A and NCgl2107-B, respectively) containing upstream and downstream regions of the NCgl2107 gene; two pairs of DNA fragments of 381 bp and 377 bp (NCgl2108-A and NCgl2108-B, respectively) containing upstream and downstream regions of the NCgl2108 gene; and two DNA fragments of DNA fragments of 356 bp and 374 bp (NCgl2986-A and NCgl2986-B, respectively) containing upstream and downstream regions of the NCgl2986 gene were obtained. The DNA fragments amplified by the PCR were conjugated to the pDZ plasmid (Korean Patent No. 10-0924065) using an Infusion Cloning Kit (Invitrogen), transformed into *E. coli* DH5a, and then plated on an LB solid medium containing kanamycin (25 mg/L). After selecting colonies transformed with the plasmids in which the desired genes are inserted through the PCR, plasmids were obtained using a plasmid extraction method conventionally known in the art. The thus-obtained plasmids were designated as pDZ-ΔNCgl1480, pDZ-ΔNCgl2107, pDZ-ΔNCgl2108, and pDZ-ΔNCgl2986, respectively. In pDZ-ΔNCgl1480, a 1672 bp gene fragment of the NCgl1480 gene was deleted; in pDZ-ΔNCgl2107, a 1026 bp gene fragment of the NCgl2107 gene was deleted; in pDZ-ΔNCgl2108, a 576 bp gene fragment of the NCgl2108 gene was deleted; and in pDZ-ΔNCgl2986, a 1092 bp gene fragment of the gene NCgl2986 was deleted.

Example 6: Production and Evaluation of Cell Wall Hydrolysis-Associated Protein Gene-Inactivated Strain Derived from Lysine-Producing Strain KCCM11016P Based on KCCM11016P, the representative L-lysine-producing strain of the genus *Corynebacterium*, the cell wall hydrolysis-associated protein gene-inactivated strain selected from the above was prepared and evaluation of its lysine productivity was attempted.

Each of the 4 recombinant plasmids (pDZ-ΔNCgl1480, pDZ-ΔNCgl2107, pDZ-ΔNCgl2108, and pDZ-ΔNCgl2986) produced in Example 5 was transformed into *Corynebacterium glutamicum* KCCM11016P by an electric pulse method, and strains wherein the target gene was inactivated by homologous recombination were prepared by a PCR method. The prepared inactivated strains were named KCCM11016P::ΔNCgl1480, KCCM11016P::ΔNCgl2107, KCCM11016P::ΔNCgl2108, and KCCM11016P::ΔNCgl2986, respectively.

Each of the 4 strains and a control strain were inoculated in a corner-baffled flask (25 mL) containing 25 mL of the following seed medium, and was cultured while shaking at 30° C. and 200 rpm for 20 hours. Thereafter, the seed culture (1 mL) was inoculated in a corner-baffled flask (1 mL) containing 24 mL of the following production medium, and was cultured while shaking at 37° C. and 200 rpm for 96 hours. The composition of each of the seed medium and the production medium is as follows.

<Seed Medium (pH 7.0)>

20 g of glucose, 10 g of $(NH_4)_2SO_4$, 10 g of peptone, 5 g of yeast extract, 1.5 g of urea, 4 g of $KH_2PO_4$, 8 g of $K_2HPO_4$, 0.5 g of $MgSO_4.H_2O$, 100 μg of biotin, 1000 μg of thiamine HCl, 2000 μg of calcium-pantothenate, 2000 μg of nicotinamide (based on 1 L of distilled water)

<Production Medium (pH 7.0)>

100 g of glucose, 40 g of $(NH_4)_2SO_4$, 2.5 g of soybean protein, 5 g of corn steep solid, 3 g of urea, 1 g of $KH_2PO_4$, 0.5 g of $MgSO_4.H_2O$, 100 μg of biotin, 1000 μg of thiamine HCl, 2000 μg of calcium-pantothenate, 3000 μg of nicotinamide, 30 g of $CaCO_3$ (based on 1 L of distilled water)

Upon completion of the cultivation, L-lysine concentrations were analyzed using HPLC, and the concentrations are shown in Table 4 below. The results in Table 4 are the results of three repeated experiments, and the productivity was evaluated based on the average value.

TABLE 4

| | Lysine (g/L) | | | |
|---|---|---|---|---|
| | Batch 1 | Batch 2 | Batch 3 | Average |
| KCCM11016P | 42.7 | 42.6 | 43.0 | 42.8 |
| KCCM11016P-ΔNCgl1480 | 44.3 | 44.1 | 44.0 | 44.1 |
| KCCM11016P-ΔNCgl2107 | 45.1 | 44.9 | 45.2 | 45.1 |
| KCCM11016P-ΔNCgl2108 | 48.1 | 48.3 | 48.0 | 48.1 |
| KCCM11016P-ΔNCgl2986 | 49.3 | 49.1 | 49.2 | 49.2 |

As a result, as shown in Table 4 above, the lysine productivity of the strain wherein each of the NCgl1480, NCgl2107, NCgl2108, and NCgl2986 genes was inactivated increased to 3.2%, 5.4%, 13%, and 15%, respectively, compared to that of the parent strain KCCM11016P.

These results suggest that the L-lysine productivity can be improved by inactivating proteins involved in cell wall hydrolysis, which may cause cell fusion in a microorganism of the genus *Corynebacterium*.

Accordingly, experiments were conducted as below to determine whether or not similar effects can be exhibited in a case where the proteins involved in cell wall hydrolysis are inactivated in various microorganisms of the genus *Corynebacterium.*

Example 7: Production and Evaluation of Cell Wall Hydrolysis-Associated Protein-Inactivated Strains Derived from L-Lysine-Producing Strain KCCM10770P In order to examine whether the effects of inactivation of cell wall hydrolysis-associated proteins in the L-lysine-producing strain *Corynebacterium glutamicum* KCCM10770P (Korean Patent No. 10-0924065) having an enhanced lysine biosynthetic pathway are similar to the experimental results of Example 6, strains in which each of the 4 proteins involved in cell wall hydrolysis was inactivated was prepared in the same manner as described in Example 6. The prepared strains were named KCCM10770P::ΔNCgl1480, KCM10770P::ΔNCgl2107, KCCM10770P::ΔNCgl2108, and KCM10770P::ΔNCgl2986. The L-lysine productivity was compared therebetween.

In order to compare the lysine productivity of the strains above, the strains and a control strain were cultured in the same manner as in Example 6. Upon completion of the cultivation, the L-lysine concentrations analyzed using HPLC are shown in Table 5 below. The results in Table 5 are the results of three repeated experiments, and the productivity was evaluated based on the average value.

TABLE 5

| | Lysine (g/L) | | | |
|---|---|---|---|---|
| | Batch 1 | Batch 2 | Batch 3 | Average |
| KCCM10770P | 46.0 | 46.3 | 46.1 | 46.1 |
| KCCM10770P-ΔNCgl1480 | 47.3 | 47.1 | 47.0 | 47.1 |
| KCCM10770P-ΔNCgl2107 | 48.0 | 48.2 | 48.1 | 48.1 |
| KCCM10770P-ΔNCgl2108 | 51.7 | 51.9 | 51.6 | 51.7 |
| KCCM10770P-ΔNCgl2986 | 53.1 | 52.9 | 52.1 | 52.7 |

As a result, as shown in Table 5 above, the lysine productivity of the strain wherein each of the NCgl1480, NCgl2107, NCgl2108, and NCgl2986 genes was inactivated increased to 2.2%, 4.3%, 12.1%, and 14.2%, respectively, compared to that of the parent strain KCCM10770P.

Accordingly, it was found that in *Corynebacterium glutamicum* KCCM10770P (Korean Patent No. 10-0924065), the L-lysine productivity can also be improved by inactivating proteins involved in cell wall hydrolysis in the same manner as in Example 6.

Example 8: Production and Evaluation of Cell Wall Hydrolysis-Associated Protein-Inactivated Strains Derived from L-Lysine-Producing Strain KCCM11347P In order to examine the effects of inactivation of cell wall hydrolysis-associated proteins in the L-lysine-producing strain *Corynebacterium glutamicum* KCCM11347P (the microorganism had been designated as KFCC10750 and re-deposited with the international depository institution under the Budapest Treaty, and was then designated the deposit accession number of KCCM11347P; Korean Patent No. 10-0073610) prepared by artificial modification, strains in which each of the 4 proteins involved in cell wall hydrolysis was inactivated was prepared in the same manner as described in Example 6. The prepared strains were named KCCM11347P::ΔNCgl1480, KCCM11347P:ΔNCgl2107, KCCM11347P::ΔNCgl2108, and KCCM11347P:ΔNCgl2986. The L-lysine productivity was compared therebetween.

In order to compare the lysine productivity of the strains above, the strains and a control strain were cultured in the same manner as in Example 6. Upon completion of the cultivation, the L-lysine concentrations were analyzed using HPLC, and are shown in Table 6 below. The results in Table 6 are the results of three repeated experiments, and the productivity was evaluated based on the average value.

TABLE 6

| | Lysine (g/L) | | | |
| --- | --- | --- | --- | --- |
| | Batch 1 | Batch 2 | Batch 3 | Average |
| KCCM11347P | 38.2 | 38.6 | 38.3 | 38.4 |
| KCCM11347P-ΔNCgl1480 | 39.0 | 39.4 | 39.1 | 39.2 |
| KCCM11347P-ΔNCgl2107 | 39.1 | 39.5 | 39.3 | 39.3 |
| KCCM11347P-ΔNCgl2108 | 39.8 | 40.2 | 39.9 | 42.9 |
| KCCM11347P-ΔNCgl2986 | 39.9 | 40.3 | 40.1 | 43.9 |

As a result, as shown in Table 6 above, the lysine productivity of the strain wherein each of the NCgl1480, NCgl2107, NCgl2108, and NCgl2986 genes was inactivated increased to 2%, 2.4%, 11.7%, and 14.4%, respectively, compared to that of the parent strain KCCM11347P.

Accordingly, it was found that in *Corynebacterium glutamicum* KCCM11347P (Korean Patent No. 10-0073610), the L-lysine productivity can also be improved by inactivating proteins involved in cell wall hydrolysis in the same manner as in Examples 6 and 7.

Example 9: Production and Evaluation of Cell Wall Hydrolysis-Associated Protein-Inactivated Strains Derived from L-Lysine-Producing Strain CJ3P In order to examine whether the effects of inactivation of cell wall hydrolysis-associated proteins in *Corynebacterium glutamicum* CJ3P (Binder et al. Genome Biology 2012, 13:R40), which produces L-lysine by introducing 3 kinds of modifications [pyc(P458S), hom(V59A), and lysC(T311I)] in wild-type *Corynebacterium glutamicum*, are similar to the experimental results of Examples 6, 7, and 8, strains in which each of the 4 proteins involved in cell wall hydrolysis was inactivated were prepared in the same manner as described in Example 6. The prepared strains were named CJ3P::ΔNCgl1480, CJ3P::ΔNCgl2107, CJ3P::ΔNCgl2108, and CJ3P::ΔNCgl2986. The L-lysine productivity was compared therebetween.

In order to compare the lysine productivity of the strains above, the strains and a control strain were cultured in the same manner as in Example 6. Upon completion of the cultivation, the L-lysine concentrations analyzed using HPLC are shown in Table 7 below. The results in Table 7 are the results of three repeated experiments, and the productivity was evaluated based on the average value.

TABLE 7

| | Lysine (g/L) | | | |
| --- | --- | --- | --- | --- |
| | Batch 1 | Batch 2 | Batch 3 | Average |
| CJ3P | 7.8 | 8.0 | 7.9 | 7.9 |
| CJ3P-ΔNCgl1480 | 8.3 | 8.0 | 8.1 | 8.1 |
| CJ3P-ΔNCgl2107 | 8.0 | 7.9 | 8.1 | 8.0 |
| CJ3P-ΔNCgl2108 | 8.8 | 8.9 | 9.0 | 8.9 |
| CJ3P-ΔNCgl2986 | 9.1 | 9.2 | 9.2 | 9.2 |

As a result, as shown in Table 7 above, the lysine productivity of the strain wherein each of the NCgl1480, NCgl2107, NCgl2108, and NCgl2986 genes was inactivated increased to 3%, 1.3%, 12.7%, and 16%, respectively, compared to that of the parent strain CJ3P.

Accordingly, it was found that in *Corynebacterium glutamicum* CJ3P, the L-lysine productivity can also be improved by inactivating proteins involved in cell wall hydrolysis in the same manner as in Examples 6, 7, and 8.

Example 10: Production and Evaluation of Cell Wall Hydrolysis-Associated Protein-Simultaneously Inactivated Strain Derived from L-Lysine-Producing Strain KCCM11016P After confirming from the Examples above that the L-lysine productivity was increased when each of the proteins involved in cell wall hydrolysis was inactivated in the L-lysine-producing strain *Corynebacterium*, identification was attempted as to whether the L-lysine productivity would be also increased when the 2 relevant proteins were simultaneously inactivated.

Therefore, the following experiment was carried out to confirm the effect of simultaneous inactivation of proteins involved in cell wall hydrolysis in the L-lysine-producing strain *Corynebacterium*. The strain in which two types of the protein genes (NCgl2108 and NCgl2986) involved in cell wall hydrolysis, which are highly effective in enhancing L-lysine productivity when each of the proteins is deficient, were simultaneously inactivated was prepared in the same manner as in Example 6. The prepared strain was designated as KCCM11016P::ΔNCgl2108/ΔNCgl2986. The L-lysine productivity was compared.

In order to compare the L-lysine productivity of the strain above, the strain and a control strain were cultured in the same manner as in Example 6. Upon completion of the cultivation, the L-lysine concentrations analyzed using HPLC are shown in Table 8 below. The results in Table 8 are the results of three repeated experiments, and the productivity was evaluated based on the average value.

TABLE 8

| | Lysine (g/L) | | | |
| --- | --- | --- | --- | --- |
| | Batch 1 | Batch 2 | Batch 3 | Average |
| KCCM11016P | 43.4 | 43.1 | 43.2 | 43.2 |
| KCCM11016P-ΔNCgl2108/ΔNCgl2986 | 52.6 | 52.4 | 52.7 | 52.6 |

As a result, as shown in Table 8, the lysine productivity of the strain wherein the NCgl2108 and NCgl2986 genes were simultaneously inactivated was increased to 21.6%, compared to that of the parent strain KCCM11016P.

This result suggests that the L-lysine productivity can be improved even when not only one protein but also two or more proteins involved in cell wall hydrolysis were simultaneously inactivated in a microorganism of the genus *Corynebacterium*.

In this regard, the strain above, KCCM11016P-ΔNCgl2986, was named CA01-2292. CA01-2292 was deposited with the Korean Culture Center of Microorganisms (KCCM), an international depository institution, under the Budapest Treaty, and was then designated the deposit accession number of KCCM11627P.

Based on these results, it was confirmed that the L-lysine-producing strains had the effect of enhancing the L-lysine productivity by regulating cell lysis during the fermentation in which the proteins involved in cell wall hydrolysis were inactivated in comparison with their endogenous activity. Additionally, it was also confirmed that the L-lysine productivity can be improved when not only one but also two or more proteins involved in cell wall hydrolysis were simultaneously inactivated, thereby providing the novel strain producing L-lysine.

While the present disclosure has been described with reference to particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for preparing L-Iysine, comprising:

(i) culturing a microorganism of the genus *Corynebacterium* in a culture medium wherein the microorganism is capable of producing L-lysine, and the microorganism is modified to have an inactivated N-acetylmuramoyl-L-alanine amidase compared to an unmodified microorganism, wherein the N-acetylmuramoyl-L-alanine amidase comprises the amino acid sequence of SEQ ID NO:4, and wherein the modification is carried out by deleting all or a part of the entire endogenous gene encoding the N-acetylmuramoyl-L-alanine amidase; and (ii) recovering L-lysine from the culture medium or the microorganism.

2. The method of claim 1, wherein the microorganism of the genus *Corynebacterium* is *Corynebacterium glutamicum.*

* * * * *